United States Patent
Otto-Nagels

[19]

[11] Patent Number: 5,900,374
[45] Date of Patent: May 4, 1999

[54] CELL CULTURE HARVESTING DEVICE

[75] Inventor: Hans Otto-Nagels, Bovenden, Germany

[73] Assignee: Heraeus Instruments GmbH & Co. KG, Hanau, Germany

[21] Appl. No.: 08/959,488

[22] Filed: Oct. 28, 1997

[30] Foreign Application Priority Data

Oct. 29, 1996 [DD] German Dem. Rep. .......... 196 44 761

[51] Int. Cl.$^6$ ............................... C12M 3/00; A47L 1/00
[52] U.S. Cl. .................. 435/379; 435/299.2; 435/304.1; 435/308.1; 435/261; 128/757; 15/220.2
[58] Field of Search .............................. 435/283.1, 299.2, 435/304.1, 308.1, 309.2, 378, 379, 395, 410, 261; 128/757; 15/211, 220.2

[56] References Cited

U.S. PATENT DOCUMENTS

| | | | |
|---|---|---|---|
| 4,004,981 | 1/1977 | Hurni et al. | 195/127 |
| 4,556,639 | 12/1985 | Izawa et al. | 435/284 |
| 4,810,652 | 3/1989 | Witt | 435/296 |
| 4,921,614 | 5/1990 | Frickman et al. | 210/695 |
| 5,422,273 | 6/1995 | Garrison et al. | 435/296 |
| 5,515,570 | 5/1996 | Muscroft | 15/220.2 |

FOREIGN PATENT DOCUMENTS

WO 85/01514  4/1985  WIPO .

OTHER PUBLICATIONS

Nunc GmbH Catalog, Dec. 1995, Nos. 179693 and 179707.
Baxter Diagnostics, Inc., Scientific Products Division, 1994/95 Catalog, Nos. T4206–1, T4130–56, 57, 58, T4136–36, 37 and T4160–157.

*Primary Examiner*—David A. Redding
*Attorney, Agent, or Firm*—Workman, Nydegger & Seeley

[57] ABSTRACT

The invention concerns a cell culture harvesting device consisting of a scraper head with a blade and a guide strip, the scraper head and the guide strip being connected with one another only by magnetic attraction. The magnetic attraction is achieved by the fact that one of the ends of the scraper head and the guide strip which are turned toward one another have a magnet and the other has either a magnet or a material which can be magnetized by the magnet of the respective counterpart. In this way, the scraper head and the guide strip can be moved synchronously and in parallel at a distance from one another. This has the advantage that the scraper head can be placed into the cell culture vessel before a cell culture is started and can be sterilized together with it thereby eliminating the risk of contamination due to a cell culture harvesting device later being placed into the cell culture vessel. Furthermore, the scraper head can have a net-like collection container arranged on it which collects the cells lifted off the growth surface of the cell culture vessel in a manner that avoids damage to the cells.

15 Claims, 2 Drawing Sheets

CELL CULTURE HARVESTING DEVICE

BACKGROUND OF THE INVENTION

1. The Field of the Invention

The invention concerns a cell culture harvesting device with a scraper head having a blade with a cutting edge and a guide strip to move the scraper head.

2. Related Applications

Foreign priority benefits under Section 119 of Title 35 of the United States Code of German Utility Model Application No. 196 44 761.5, filed Oct. 29, 1996, incorporated herein by reference, are claimed for this application.

3. The Relevant Technology

Cell culture harvesting devices in the form of scrapers which have a scraper head and a rod-shaped stem, which is sometimes also withdrawable, are well-known and common laboratory equipment. Typically, the dimensions of the scraper head are adapted to the neck openings of common cell culture flasks, since it must be introduced into the cell culture vessel through this opening. Cultured cells grow and adhere to the curved wall of roller bottle-type cell culture vessels and to the flat-surfaced wall forming the floor in cell culture vessels having relatively flat parallel walls. For purposes of this disclosure, the term "floor" is used to refer to the growth surface of a cell culture vessel, i.e., the curved wall of roller bottle-type cell culture vessels or the flat-surfaced floor wall of other types of cell culture vessels, where cells grow and adhere and from which such cells need to be harvested, i.e., removed, by the cell culture harvesting devices in accord with the present invention as disclosed herein. Accordingly, conventional cell culture harvesting devices operate to lift the adherent cells on the floor of the cell culture vessel off the surface of the floor by the scraper head which is moved by the guide strip.

For example, cell culture scrapers of this kind are described in the 1995–1996 laboratory catalog of the company Nunc GmbH under the numbers 179693 and 179707, and in the catalog of the company Baxter Diagnostics, Inc., Scientific Products Division under the numbers T4206-1, T4130-56, 57, 58, T4136-36, 37, and T4160-157. In some cases, the scraper head can be rotated with respect to the guide strip, so that a greater area of cell culture growth surface can be reached.

Cell removal devices for removing multiple cell cultures are also known from U.S. Pat. No. 4,004,981. The devices are utilized with cylindrical cell culture vessels having a number of circular cell culture growth surfaces stacked at a distance on top of one another parallel to the cylindrical front surfaces. The cell culture scraper has at least one scraper head which is circular in cross section and which is placed onto the circular cell culture growth surfaces. Rotating motions of the cell culture scraper and/or the cell culture growth surfaces effects lifting of the cells off the growth surface or pushing of the cells to the edge of the growth surface. If the cell culture scraper has several scraper heads, then several cell culture growth surfaces can be processed/harvested simultaneously.

A problem encountered during cell culturing is the risk of contamination of the cells and/or the cell culture vessel during the process. To reduce the risk of contamination by introduction of cell culture scrapers of the previously described type into the cell culture vessel, it is necessary to use sterile scrapers. Therefore, some of these scrapers are offered already sterilized in individual packages, while others must be sterilized before use in a separate sterilization process. Introducing the scraper into the cell culture vessel and placing it onto the cell culture growth surface requires careful and precise handling on the part of the operating personnel, since otherwise the cells can easily be mechanically damaged or even destroyed due to insufficient care and attention. Especially with roller bottle-type cell culture vessels, cell culture harvesting with known cell culture scrapers is relatively ineffective because reaching all areas of the growth surface is technically very difficult and/or depends too much on the skill, care, and attention of operating personnel. Another problem with conventional cell scraper devices is seen in the fact that, depending on the scraper head's angle of attack, the cells which are lifted can accumulate in front of or behind the scraper head in such a way that the cells are distorted and/or damaged in the process.

Moreover, cell culture harvesting procedures are known which lift the adherent cells from the growth surface of the cell culture vessel by adding chemical loosening fluids. Typically, knocking or vibrating the growth surface is used to promote this process. U.S. Pat. No. 4,556,639 describes such a cell culture harvesting procedure and a device suitable for implementation thereof. According to this procedure, the cell culture is first placed in a flat cell culture vessel and is subjected to the action of an enzyme-containing solution which reduces the adhesion of the cells to the growth surface of the cell culture vessel. Next, the cell culture vessel is placed into the receptacle of an apparatus which effects movement of the prepared cell culture growth surface in the perpendicular and/or parallel direction to the growing surface. The movement can be produced by ultrasound. The receptacle with the cell culture vessel is also moved parallel to the plane of the growth surface in a direction which is opposite to the movement already described. Due to the actions of the enzyme solution and the multiple-direction movements of the cell culture vessel, the cells are dislodged such that these can be suitably removed and spatially concentrated by withdrawing the enzyme-containing solution containing the cells from the cell culture vessel. Manipulation according to the procedure described is labor-intensive and requires the special apparatus. In addition, the procedure is not very flexible due to the combination of chemical and physical methods.

Therefore, it is the task of the invention to eliminate the disadvantages encountered with conventional cell culture harvesting apparatus and methods. In particular, it would be an advancement to provide cell culture harvesting devices that are simple, cost-effective, and versatile and which minimize the risk of contamination and the potential for distorting and/or damaging cultured cells during the harvesting process.

SUMMARY AND OBJECTS OF THE INVENTION

It is an object of the present invention to provide cell culture harvesting devices that are simple, cost-effective, and versatile and that can be used effectively with all types of cell culture vessels.

It is a further object of the present invention to provide cell culture harvesting devices which minimize the risk of contamination to the cells and/or the cell culture vessel during the harvesting process.

Yet another object of the present invention to provide cell culture harvesting devices which minimize the potential for distorting and/or damaging cultured cells during the harvesting process.

These and other objects and features of the present invention will become more fully apparent from the following description and appended claims, or may be learned by the practice of the invention as set forth hereinafter.

The present invention solves these problems by providing cell culture harvesting devices which use magnetic attraction to guide a scraper head, positioned within a cell culture vessel, with a guide strip positioned outside of the cell culture vessel. In particular, one of the components, either the scraper head or the guide strip has a magnet turned toward the respective other component, and the respective other component has either a second correspondingly turned magnet or a magnetizable material turned toward the first magnet such that magnetic attraction permits the scraper head to be guided by the guide strip. In this manner, the scraper head is positioned inside the cell culture vessel and the guide strip is positioned outside of the cell culture vessel and the necessary connection is effected only by the magnetic attraction. Accordingly, the cell culture harvesting devices in accord with the present invention are essentially two-part tools, the scraper head being moved by the guide strip without these two parts being mechanically connected with one another. If desired, the guide strip can be placed against the outside surface of the cell culture vessel floor opposite the scraper head arranged on the inside surface of the floor where the guide strip will be held by magnetic attraction. Alternatively, if desired, the position of the scraper head can also be secured during the cell cultivation process by a mechanical holder placed inside the cell culture vessel, which is made in such a way that the holder easily releases the scraper head when desired. In addition, if desired, a single guide strip can be used to secure and/or effect movement of several scraper heads in desired positions within a cell culture vessel.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1A:
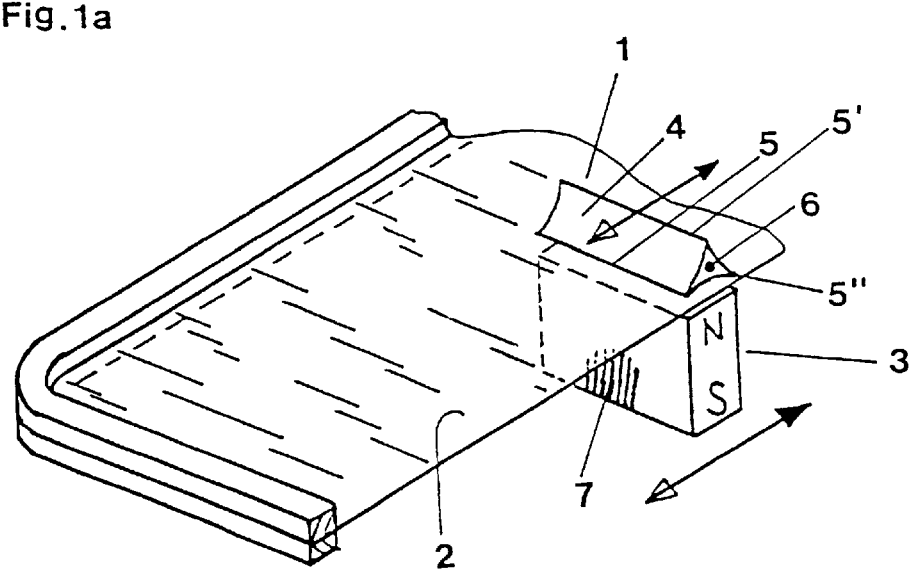
FIG. 1a shows a preferred embodiment of a cell culture harvesting device in accord with the present invention positioned on the floor of a cell culture vessel.

The invention concerns a cell culture harvesting device with a scraper head having a blade with a cutting edge and a guide strip to move the scraper head. As described above, cell culture harvesting devices in the form of scrapers which have a scraper head and a rod-shaped stem, which is sometimes also withdrawable, are well-known and common laboratory equipment. Cultured cells grow and adhere to the curved wall of roller bottle-type cell culture vessels and to the flat-surfaced wall forming the floor in cell culture vessels having relatively flat parallel walls. For purposes of this disclosure, the term "floor" is used to refer to the growth surface of a cell culture vessel, i.e., the curved wall of roller bottle-type cell culture vessels or the flat-surfaced floor wall of other types of cell culture vessels, where cells grow and adhere and from which such cells need to be harvested, i.e., removed, by the cell culture harvesting devices in accord with the present invention as disclosed herein. Accordingly, conventional cell culture harvesting devices having a scraper head and a guide strip, such as a rod or stem fixed to the scraper head, are introduced into cell culture vessels where the scraper head is then manipulated by movement of the guide strip to lift the adherent cells on the floor of the cell culture vessel off the surface of the floor. Problems with conventional cell culture harvesting devices include contamination from introduction of the devices into the cell culture vessel, difficulty in maneuvering the devices among the cells to effectively lift and collect the cells, and the occurrence of distortion and/or damage to the cells during the harvesting process.

The present invention solves these problems by providing cell culture harvesting devices which use magnetic attraction to guide a scraper head, positioned within a cell culture vessel, with a guide strip positioned outside of the cell culture vessel. In particular, one of the components, either the scraper head or the guide strip has a magnet turned toward the respective other component, and the respective other component has either a second correspondingly turned magnet or a magnetizable material turned toward the first magnet such that magnetic attraction permits the scraper head to be guided by the guide strip. In this manner, the scraper head is positioned inside the cell culture vessel and the guide strip is positioned outside of the cell culture vessel and the necessary connection is effected only by the magnetic attraction.

The cell culture harvesting devices in accord with the present invention are essentially two-part tools, the scraper head being moved by the guide strip without these two parts being mechanically connected with one another. Rather, it is only magnetic attraction which acts between them, so that the scraper head and the guide strip can be moved synchronously and in parallel at a distance from one another. This feature has the advantage that the scraper head can be placed into the cell culture vessel in a desirable location before a cell culture is started. In this manner, the scraper head can be sterilized together with the cell culture vessel and the risk of contamination from a cell culture harvesting device being subsequently introduced into the cell culture vessel is eliminated. The risk of contamination from the guide strip is also eliminated since the guide strip remains at all times outside of the cell culture vessel. If desired, the guide strip can be placed against the outside surface of the cell culture vessel floor opposite the scraper head arranged on the inside surface of the floor where the guide strip will be held by magnetic attraction. This positioning configuration is expedient, since in this way the scraper head and the guide strip are already fixed in the desired position for beginning cell culture harvesting before the cell cultivation process begins. In this positioning configuration, the scraper head cannot change its position within the cell culture vessel in an uncontrolled manner and possibly damage the cell culture in the process. This possibility is especially significant for cell culture roller bottles, since in this case the entire cell culture vessel is kept in permanent motion. Alternatively, if desired, the position of the scraper head can also be secured during the cell cultivation process by a mechanical holder placed inside the cell culture vessel, which is made in such a way that the holder easily releases the scraper head when desired. In addition, if desired, a single guide strip can be used to secure several scraper heads in desired positions within a cell culture vessel.

The magnetic attraction between the guide strip and the scraper head is achieved either by the fact that both the guide strip and the scraper head have a magnet on their ends turned toward their respective counterparts, whose polarity attracts the other magnet (north pole/south pole, north pole/south pole), or by the fact that either the guide strip or the scraper head has a magnet and the respective counterpart contains a magnetizable material on its end turned toward the magnet. The scraper head can be made as a long part whose cross section can have, for example, the shape of a triangle or a rectangle with sides curved partially inward, so that the corners of this triangle simultaneously represent the cutting edges of the scraper head. Many other geometric cross-sectional shapes adapted to the shape of the respective cell culture vessel are also possible, which either offer a cutting edge themselves, or which make possible a fixed arrangement of a blade with a cutting edge. It is advantageous if the blade, in addition to functioning as a cutter or scraper, can simultaneously be made to function as a permanent magnet or to have a magnetizable material, the latter for the case that only the guide strip is provided with a magnet. The guide strip has a shape suitable for its function.

Since metallic surfaces are toxic to cell cultures, the scraper head must be made from, or coated with, a plastic, non-toxic material. Preferably, both parts of the cell culture harvesting device, the scraper head and the guide strip, are coated with a plastic. This coating is non-toxic, and thus creates a surface which ensures optimal protection for the cell cultures, cell culture vessel parts, and operating personnel coming in contact with the cell culture harvesting device. In addition, the coating permits both the scraper head and guide strip to be moved with a minimum of friction against the growth surfaces and outside surfaces, respectively, of a cell culture vessel. Since, in principle, all tools coming in contact with the cell culture must be sterile, the plastic used for coating, especially that used for coating the scraper head, must be sterilizable by the common procedures (gamma rays, overpressure, gas, etc.) used to sterilize cell culture vessels. One plastic which fulfills these conditions is poly (tetrafluoroethylene) (PTFE), however, other plastics are also possible, such as polycarbonate, for example, and may also be utilized.

Handling of the cell culture harvesting device is facilitated by the fact that the guide strip has a handle or, at least, gripping surfaces. The gripping surfaces may lie on the end of the guide strip opposite the magnet or the end having the magnetizable material. If desired, the gripping surfaces can be colored and/or ribbed. Alternatively, the guide strip can be installed or inserted in a table for setting cell culture vessels on, so that cell culture harvesting only requires moving a cell culture vessel with a scraper head back and forth on the surface of the table.

To catch or collect the cells lifted off the growth surface of the cell culture vessel by moving the scraper head, the scraper head may optionally have a net-like container arranged on it. In a preferred embodiment, the container extends over the length of the scraper head and the opening of the container is at least as long as the cutting edge of the blade. This container is arranged on the upward-facing side of the scraper head while the container opening is adjacent to the cutting edge of the blade, so that the cells lifted off the growth surface by movement of the blade automatically collect in the collection container. In this manner, damage to the cells by distorting them or by touching the cells which are already resting loose on the growth surface of the cell culture vessel when a neighboring batch is harvested within the cell culture harvesting device is avoided. Furthermore, this collection container substantially facilitates the removal of the harvested cells. The outside dimensions of the collection container are naturally determined by the size of the openings in the cell culture vessel.

Sample embodiments of the invention are explained in detail below using the drawings. FIG. 1a shows a simple embodiment of the invention. The scraper head 1 is shown positioned on the inside surface of a floor 2 from which cells are to be harvested. The floor 2 separates the scraper head 1 from its guide strip 3, which is made as a magnet. In this embodiment, the scraper head 1 has the shape of a long rod with a triangular cross section. Preferably, as shown, the sides 4 of the triangle are not straight but rather are curved inward, so that three possible cutting edges 5, 5', 5" result which are suitable to act as a blade. When the scraper head 1 is moved parallel to the floor 2 and perpendicular to one of the three cutting edges 5, 5', 5", the cells are lifted off the floor 2 by the cutting edge. No additional blade is required in this design. In this embodiment, since all three edges are adapted to be a cutting edge, it does not matter which two of the three cutting edges 5, 5', 5" of the scraper head 1 are placed upon the floor 2. This feature demonstrates this design's simple and flexible manipulation.

FIG. 1a also shows a rod-shaped magnet 6 in the center of the scraper head 1, which extends inside over the entire length of the scraper head 1. This magnet 6 has its poles arranged so that a magnetic field is formed between it and the magnet or magnets (not shown here) inside the guide strip 3. The polarity of the magnets in the guide strip 3 is indicated by the letters N and S in FIG. 1a. The guide strip 3 is of the same length as the scraper head 1. Preferably, as shown, the guide strip has gripping surfaces 7 on the sides to facilitate gripping and moving of the guide strip. The illustrated guide strip 3 is shown having a rectangular shape, however, it will be appreciated that any shape may be used so long as stable and secure magnetic attraction is maintained with the entire length of the scraper head, which may also have different shapes, as described below.

Figure 1B:
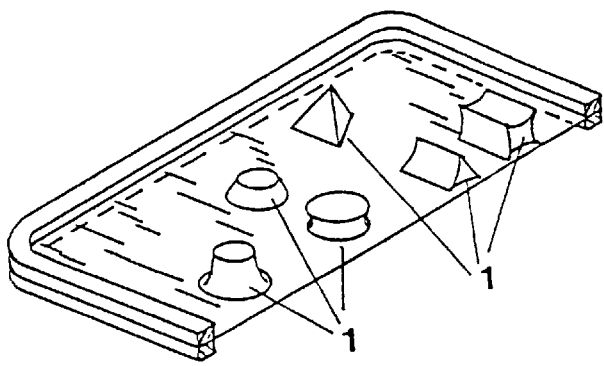
FIG. 1b shows various preferred designs of the shape of the scraper head of a cell culture harvesting device in accord with the present invention positioned on the floor of a cell culture vessel.
Figure 2:
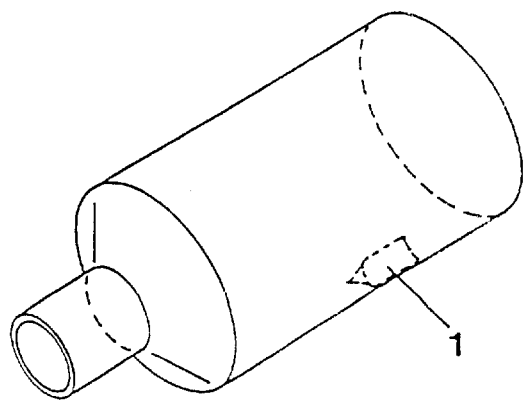
FIG. 2 shows a cell culture roller bottle having a scraper head portion of a cell culture harvesting device in accord with the present invention positioned inside the cell culture roller bottle.

FIG. 1b shows several scraper heads 1 with different geometries on the floor 2 of a cell culture vessel. The selection of geometry is guided by the respective shape of the cell culture vessel in which the scraper head will be used. A scraper head 1 having a triangular profile is suitable for a roller bottle, as shown in FIG. 2. This design makes it possible, without special effort, to harvest all cells on the lateral surface of the roller bottle by moving the scraper head 1 with a guide strip lying outside against the roller bottle.

Figure 3:
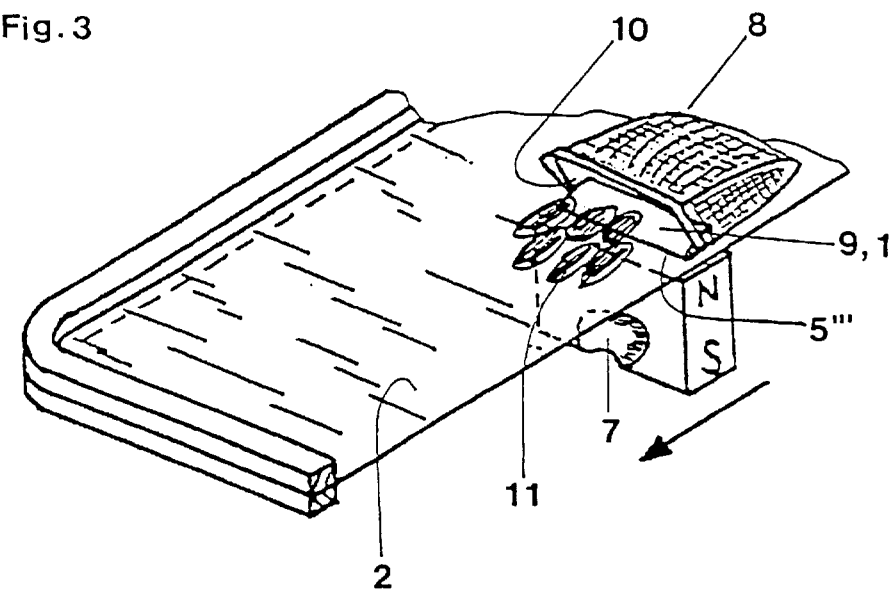
FIG. 3 shows an alternative preferred embodiment of a cell culture harvesting device comprising a collection container in accord with the present invention positioned on the floor of a cell culture vessel.

The cell culture harvesting device shown in FIG. 3 describes an embodiment which has been expanded by adding a collection container 8. The scraper head 1 is represented by the blade 9 with only one cutting edge 5'''. Blade 9 may be a permanent magnet or may consist of magnetizable material. The upward side of blade 9 has a net-like collection container 8 arranged on it. The collection container 8 has an opening 10 directed toward the cutting edge 5'''. The mesh size of the net-like collection container 8 is preferably in the range of about 1–20 µm, depending on the type of cell to be harvested. Moving the scraper head 1, which is in the form of the blade 9 and which is equipped with the collection container 8, in the direction of the arrow, parallel to the floor 2 and perpendicular to the cutting edge 5''', effects collection of the lifted cells 11—represented here as irregular, round particles—within the collection container 8. Scraper head 1 is moved by operating the guide strip 3, which is separated from the scraper head 1 by the floor 2, and which has all the same features as the guide strip 3 in FIG. 1a.

Figure 4:
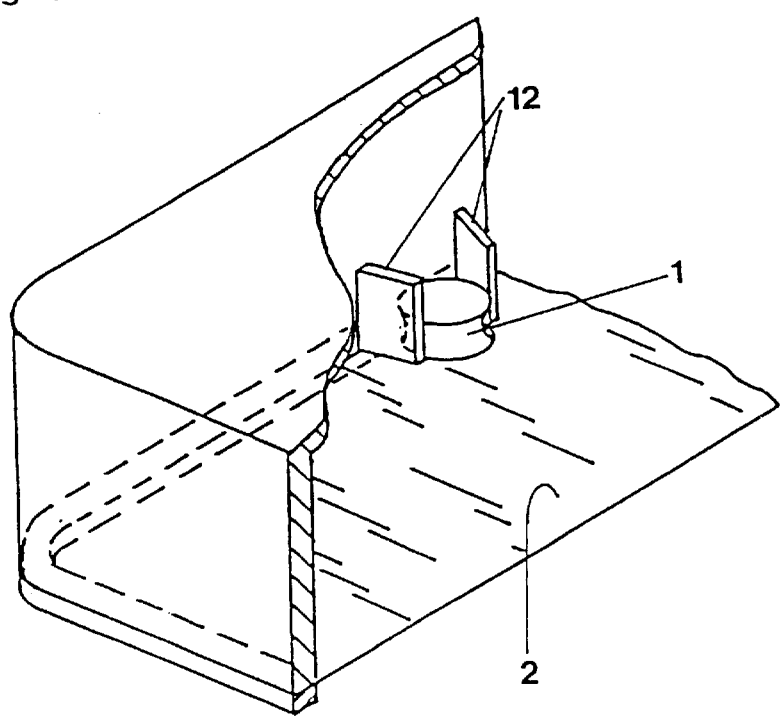
FIG. 4 shows another alternative preferred embodiment of a cell culture harvesting device comprising a holder for the scraper head positioned on the edge of the floor of the cell culture vessel, which is shown partially cut away for illustration purposes.

FIG. 4 shows a scraper head 1 that is held in a stable and secure position within the cell culture vessel by a holder 12 located inside a cell culture vessel at the edge of the floor 2. Here, the scraper head 1 has a cylindrical geometry, with an inward curved lateral surface. The holder 12 consists, for example, of two elastic plastic wings, which are adjusted at such at an angle to one another starting from the edge of the floor 2 that they limit and hold the scraper head 1. When a guide strip 3 (as shown in FIG. 1) is placed directly opposite the scraper head on the outside of the floor 2, the scraper head 1 is ready to be moved due to the magnetic attraction. Because of the elasticity of the holder 12, the scraper head 1 is readily released from the position within the holder when the scraper head 1 is caused to move synchronously with the movement of the guide strip 3.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cell culture harvesting device comprising:
    (a) a scraper head having a blade with a cutting edge for lifting cells to be harvested from a growth surface of a cell culture vessel; and
    (b) a guide strip to effect movement of the scraper head, said guide strip being connected with said scraper head by magnetic attraction such that said scraper head may be synchronously moved upon an inside surface of said cell culture vessel by directed movement of said guide strip upon an outside surface of said cell culture vessel; wherein one of said scraper head and guide strip comprises a first magnet and the other of said scraper head and guide strip comprises a second magnet or a magnetizable material suitably oriented to said first magnet to thereby provide said magnetic attraction connecting said scraper head and said guide strip; and
    (c) collecting means mounted on said scraper head for collecting the cells lifted by said blade.

2. The cell culture harvesting device according to claim 1 wherein said blade of said scraper head comprises a magnet or a magnetizable material.

3. The cell culture harvesting device according to claim 1 wherein said scraper head has a surface coated with a sterilizable plastic material.

4. The cell culture harvesting device according to claim 3 wherein said sterilizable plastic material is poly(tetrafluoroethylene).

5. The cell culture harvesting device according to claim 1 wherein said guide strip further comprises a gripping surface to facilitate directed movement of said guide strip by hand.

6. The cell culture harvesting device according to claim 1 wherein said collecting means comprises a net-like collection container for the cells harvested by movement of the scraper head, said net-like collecting container positioned on the upward-facing surface of said scraper head.

7. The cell culture harvesting device according to claim 6 wherein said net-like collection container has an opening positioned adjacent to said blade and having a length that is at least equal to the length of said blade.

8. A device for harvesting cell culture from the surface of a cell culture vessel, the device comprising:
    (a) a scraper head having a rigid blade including a forward projecting cutting edge and a sloping face that smoothly extends backward and up from the cutting edge, the cutting edge being configured to lift the cell culture from the surface of the cell culture vessel and the face being configured to receive and retain the cell culture from the cutting edge without significant damage to the cell culture; and
    (b) a guide strip wherein one of the guide strip and scraper head comprises a first magnet and the other of the scraper head and guide strip comprises a second magnet or a magnetizable material suitably oriented to the first magnet to thereby provide a magnetic attraction connecting the scraper head and the guide strip.

9. A system for harvesting cell culture comprising:
    (a) a cell culture vessel having a compartment bounded by an interior surface;
    (b) a scraper head removably disposed within the compartment of the cell culture vessel, the scraper head having a cutting edge and a first magnet or magnetizable material enclosed within a sterilizable material;
    (c) holder means for securing the scraper head in a stationary position within the compartment when the cell culture vessel is moved; and
    (d) a guide strip disposed on the exterior of the cell culture vessel, the guide strip comprising a second magnet or magnetizable material suitably oriented to the first magnet or magnetizable material so as to provide a magnet attraction between the scraper head and the guide strip.

10. A method for harvesting cell culture comprising the steps of:
    (a) positioning a scraper head within the compartment of a cell culture vessel, the compartment being bounded by an interior surface, the scraper head having a cutting edge and a first magnet or magnetizable material enclosed within a sterilizable material;
    (b) sterilizing the compartment of cell culture vessel having the scraper head disposed therein;
    (c) growing cell cultures on the interior surface of the cell culture vessel;
    (d) positioning a guide strip on the exterior of the cell culture vessel adjacent to the scraper head on the interior surface of the cell culture vessel, the guide strip comprising a second magnet or magnetizable material suitably oriented to the first magnet or magnetizable material so as to provide a magnet attraction between the scraper head and the guide strip; and
    (e) moving the guide strip on the exterior of the cell culture vessel such that the scraper head is moved so that the cutting edge thereof lifts at least a portion of the cell culture from interior surface.

11. A method as recited in claim 10, wherein the step of growing the cell cultures further comprises rotating the cell culture vessel.

12. A method as recited in claim 10, further comprising the step of releasably securing the scraper head to a holder disposed in the compartment of cell culture vessel.

13. A method as recited in claim 10, further comprising the step of positioning a plurality of scraper heads within the compartment of cell culture vessel, each of the scraper heads having a unique configuration.

14. A method for harvesting cell culture comprising the steps of:
 (a) positioning a scraper head within the compartment of a cell culture vessel, the compartment being bounded by an interior surface, the scraper head having a cutting edge and a first magnet or magnetizable material enclosed within a sterilizable material;
 (b) releasably securing the scraper head to a holder disposed in the compartment of cell culture vessel;
 (c) growing cell cultures on the interior surface of the cell culture vessel;
 (d) positioning a guide strip on the exterior of the cell culture vessel adjacent to the scraper head on the interior surface of the cell culture vessel, the guide strip comprising a second magnet or magnetizable material suitably oriented to the first magnet or magnetizable material so as to provide a magnet attraction between the scraper head and the guide strip; and
 (e) moving the guide strip on the exterior of the cell culture vessel such that the scraper head is moved so that the cutting edge thereof lifts at least a portion of the cell culture from interior surface.

15. A method as recited in claim 14, further comprising the step of sterilizing the compartment of cell culture vessel after the scraper head is secured to the holder.

* * * * *